US00PP30871P2

(12) United States Plant Patent
Boeder

(10) Patent No.: US PP30,871 P2
(45) Date of Patent: Sep. 3, 2019

(54) ***DIANTHUS* PLANT NAMED 'A12228-0'**

(50) Latin Name: *Dianthus gratianopolitanus*
Varietal Denomination: A12228-0

(71) Applicant: Armada Young Plants, De Lier (NL)

(72) Inventor: Mark Boeder, The Hague (NL)

(73) Assignee: ARMADA YOUNG PLANTS, The Hague (NL)

( * ) Notice: Subject to any disclaimer, the term of this patent is extended or adjusted under 35 U.S.C. 154(b) by 0 days.

(21) Appl. No.: 15/998,814

(22) Filed: Aug. 16, 2018

(51) Int. Cl.
*A01H 6/30* (2018.01)

(52) U.S. Cl.
USPC ..... Plt./282

(58) Field of Classification Search
USPC ..... Plt./282
See application file for complete search history.

*Primary Examiner* — Annette H Para
(74) *Attorney, Agent, or Firm* — Penny J. Aguirre

(57) ABSTRACT

A new cultivar of *Dianthus* plant named, 'A12228-0', that is characterized by its flowers that are red-pink in color and fading to a lighter pink center, its floriferous and long blooming habit and its compact plant size.

2 Drawing Sheets

Botanical classification: *Dianthus gratianopolitanus.*
Variety denomination: 'A12228-0'.

CROSS REFERENCE TO A RELATED APPLICATION

This application is co-pending with a U.S. Plant Patent Application filed for a plant derived from the same breeding program that is entitled *Dianthus* Plant Named 'A12231-0' (U.S. Plant patent application Ser. No. 15/998,813).

BACKGROUND OF THE INVENTION

The present invention relates to a new and distinct cultivar of an interspecific hybrid *Dianthus* plant, known as *Dianthus* 'A12228-0' and will be referred to hereinafter by its cultivar name, 'A12228-0'. The new cultivar represents a new herbaceous perennial grown for landscape use.

The new cultivar arose from an ongoing breeding program in De Lier, The Netherlands with the goal of developing new cultivars of *Dianthus* with compact plant habits and prolific flowering in a range of flower colors. 'A12228-0' originated as a seedling that arose from seed planted from open pollination of 'Dianturi Twinkle' (not patented). 'A12228-0' was selected as a single unique plant in April of 2015 from amongst the resulting seedlings.

Asexual propagation of the new cultivar was first accomplished using stem cuttings in April of 2015 in De Lier, The Netherlands. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'A12228-0' as a unique and distinct cultivar of *Dianthus.*

1. 'A12228-0' exhibits flowers that are red-pink in color and fading to a lighter pink center.

2. 'A12228-0' exhibits a floriferous and long blooming habit; blooming from May to September in the Netherlands.
3. 'A12228-0' exhibits a compact plant size.

The parent plant, 'Dianturi Twinkle', differs from 'A12228-0' in being taller in height and in having flowers that are less bright and less red in color. 'A12228-0' can be most closely compared to *Dianthus* cultivars 'Kahori' (not patented) and 'A12231-0'. 'Kahori' differs from 'A12228-0' in having a shorter blooming season (June to August) and flowers that are less bright in color with petals that are less overlapping. 'A12231-0' is similar to 'A12228-0' in having a compact plant habit, a prolific blooming habit, and pink flowers but differs from 'A12228-0' in being slightly less compact with a taller height and in having flower centers that are less white in color.

BRIEF DESCRIPTION OF THE DRAWINGS

The accompanying colored photographs illustrate the overall appearance and distinct characteristics of the new *Dianthus*. The photographs in the figures were taken of a plant one year in age as grown in a greenhouse in a 17-cm container in De Lier, The Netherlands.

The photograph in FIG. 1 provides a side view of a plant of 'A12228-0' in bloom.

Figure 1:
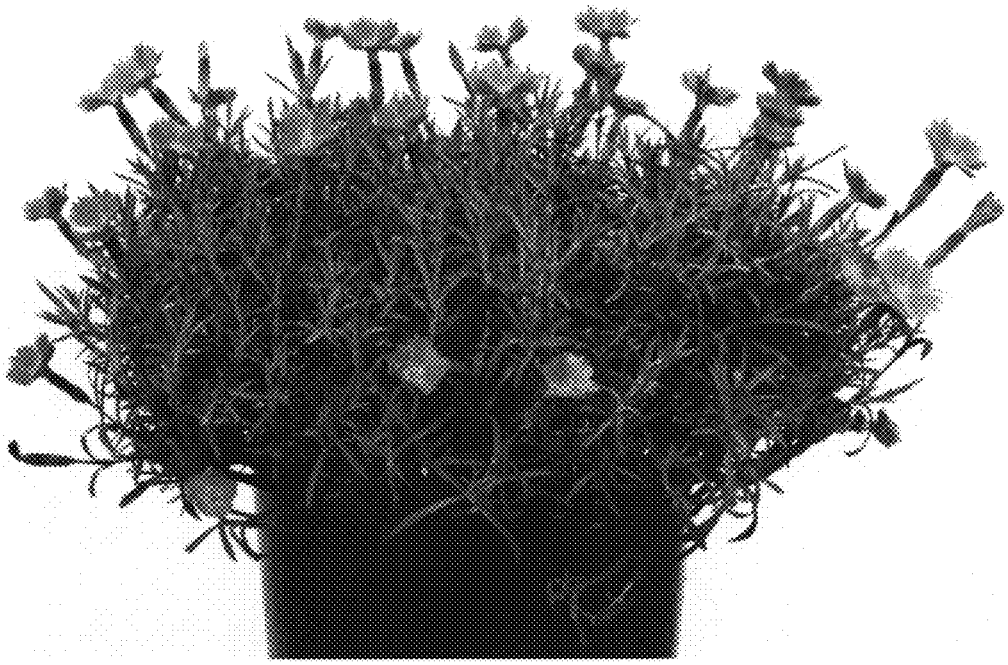
Figure 2:
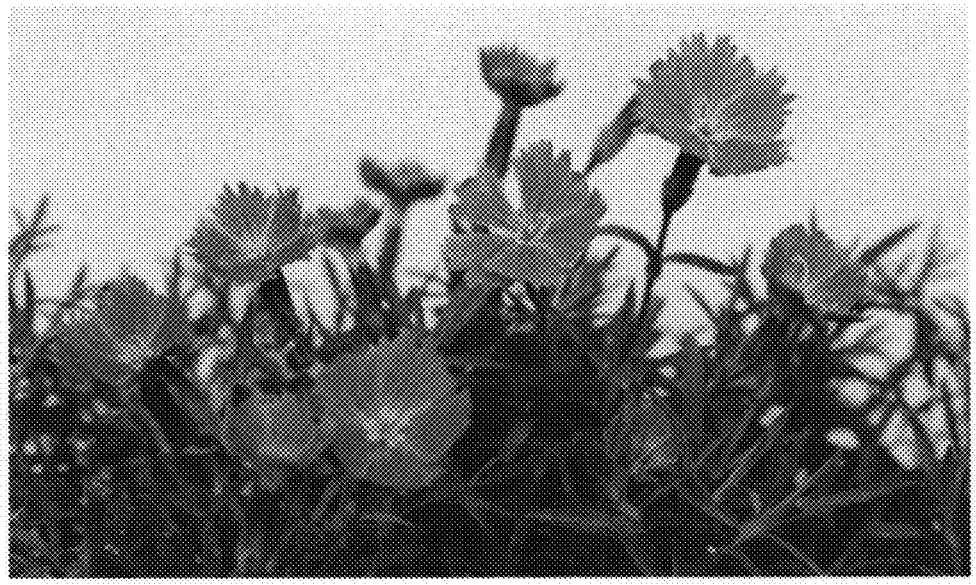

The photograph in FIG. 2 provides a close-up view of the flowers of 'A12228-0'.

Figure 3:
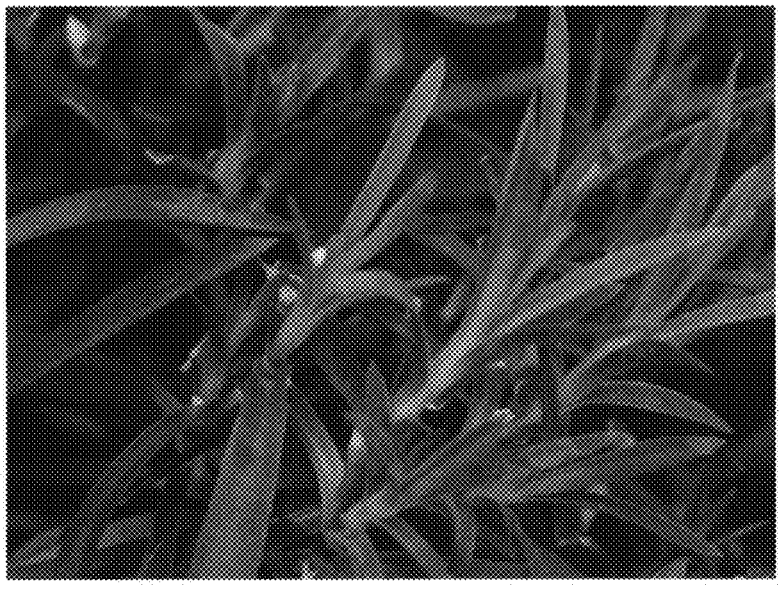

The photograph in FIG. 3 provides a close-up of the foliage of 'A12228-0'.

The colors in the photographs are as close as possible with the digital photography and printing techniques utilized and the color codes in the detailed botanical description accurately describe the colors of the new *Dianthus.*

DETAILED BOTANICAL DESCRIPTION

The following is a detailed description of plants about 1-year-in-age as grown as grown in a greenhouse in 17-cm containers in De Lier, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms continuously from May to September in The Netherlands.

*Plant type*.—Herbaceous perennial.

*Plant habit*.—Broadly spreading to spreading-upright.

*Height and spread*.—An average of 12.8 cm in height foliar, 14.5 cm in height to top of floral plane and 35.4 cm diameter.

*Hardiness*.—U.S.D.A. Zones 3 to 9.

*Diseases and pests*.—No susceptibility and resistance to diseases or pests has been observed.

*Root description*.—Fibrous and fine.

*Propagation*.—Stem cuttings.

*Root initiation*.—An average of 4 weeks.

*Root development*.—12 to 14 weeks to finish as a young plant.

*Growth rate*.—Moderate to high.

Stem description:

*Stem strength*.—Strong.

*Stem aspect*.—Held in multiple angles.

*Shape*.—Rounded.

*Stem color*.—An average of 11.9 cm in height and 1 mm in diameter.

*Stem surface*.—Matte.

*Branching habit*.—An average of 20 basal stems 6 lateral stems per basal stem.

*Internode length*.—Average of 6 mm.

Foliage description:

*Leaf division*.—Simple.

*Leaf shape*.—Narrow oblanceolate, very slightly carinate, very slightly curved.

*Leaf base*.—Decurrent.

*Leaf apex*.—Acute.

*Leaf margin*.—Entire.

*Leaf venation*.—Parallel, color; upper surface NN137A, lower surface 146B.

*Leaf attachment*.—Sessile.

*Leaf arrangement*.—Opposite.

*Leaf surface*.—Both surfaces glabrous, smooth and matte.

*Leaf number*.—An average of 14 (7 pairs) per lateral branch.

*Leaf color*.—Young upper surface; 137A, young lower surface; 137A to 137B, mature upper surface; NN137A, mature lower surface, NN137B.

*Leaf size*.—An average of 4.6 cm in length and 4.5 mm in width.

*Foliage fragrance*.—None.

Flower description:

*Inflorescence type*.—Terminal solitary flowers.

*Lastingness of inflorescence*.—About 10 days, self-cleaning.

*Fragrance*.—Faint, typical *Dianthus* scent.

*Quantity of flowers*.—Average of 40 per plant.

*Flower type*.—Rotate and solitary.

*Flower size*.—An average of 2.8 cm in diameter and 2.9 cm in length.

*Flower buds*.—An average of 1.4 cm in length and 3.5 mm in width, elliptic to oblong in shape, glabrous, smooth and very slightly glossy surface, color; 138B, base 145A, apex tinged 183A to 183B.

*Peduncle*.—An average of 1.7 cm in length and 1 mm in diameter, 137B in color, smooth, glabrous and slightly glossy surface, held straight on top of flower stem, moderately strong in strength.

*Pedicel*.—Not present.

*Petals*.—5, rotate, 1 whorl, spathulate in shape, margins irregular dentate, lower half entire, medium undulation, apex irregularly toothed and praemorse, slightly overlapping, cuneate base, both surfaces velvety, glabrous, slightly velvety, matte, an average of 3.3 cm in length and 1.5 cm in width, color; upper surface when opening marbled 59A, 59B, 61A and 68A, very base 145C, lower surface when opening marbled 185C to 185D, very base 145C, upper surface fully open marbled 60C, 60D and 61A (lightest towards centers), base 145C to 145D, lower surface fully open marbled 186A and 186B, very base 145C to 145D, upper surface venation 60C, 60D, 61A, lower surface venation 186A to 186B.

*Calyx*.—Rotate, campanulate in shape, an average of 1.8 cm in length and 4 mm in diameter.

*Sepals*.—5, rotate, 1 whorl, oblong in shape, entire margin, acute apex, fused base (lower 75% fused into a campanulate shape), an average of 1.7 cm in length and 2.5 mm in width, smooth, glabrous, matte surface, color; when opening upper surface 145A, apex tinged 185C, when opening lower surface 138B, base 145A, apex tinged 183A to 183B, fully open upper surface 144A to 144B and towards the apex 146B to 146C with very apex tinged 185C, fully open lower surface 144B, fading towards the top to 147A, apex tinged 183A.

Reproductive organs:

*Gynoecium*.—2 pistils; an average of 1.9 cm in length, style; NN155D in color, 1.7 cm in length, an average of 1.7 cm in length, stigma; pointed, curled, 72D in color, ovary; 144C in color.

*Androecium*.—Stamens; 10, filament; NN155A, fading towards the base to 157C in color, an average of 1.6 cm in length, anthers; 179D in color, narrow elliptic, dorsifixed in shape, an average of 2 mm in length, 1 mm in width, pollen; low in quantity, 156C in color.

*Fruit and seed*.—Not observed to date.

It is claimed:

1. A new and distinct cultivar of *Dianthus* plant named 'A12228-0' as herein illustrated and described.

* * * * *